United States Patent

Kohn et al.

Patent Number: 5,132,315
Date of Patent: Jul. 21, 1992

[54] THERAPEUTIC APPLICATION OF AN ANTI-INVASIVE COMPOUND

[75] Inventors: Elise C. Kohn, Olney; Lance A. Liotta, Potomac, both of Md.

[73] Assignee: The United States of America as represented by the Department of Health and Human Services, Washington, D.C.

[21] Appl. No.: 355,744

[22] Filed: May 19, 1989

[51] Int. Cl.$^5$ .............................................. A61K 31/41
[52] U.S. Cl. .................................. 514/359; 514/650; 514/648; 548/257
[58] Field of Search ............... 514/263, 863, 648, 359, 514/650; 548/257

[56] References Cited

U.S. PATENT DOCUMENTS 4,847,257 10/1962 Hupe et al. ........................ 514/863

OTHER PUBLICATIONS

Darland's Illustrated Medical Dictionary, 26th Ed., pp. 806, 805, 1985.

Primary Examiner—José G. Dees
Assistant Examiner—Deborah D. Carr
Attorney, Agent, or Firm—Birch, Stewart, Kolasch & Birch

[57] ABSTRACT

Tumor invasion and metastasis is the most life threatening aspect of cancer. Invasion and metastasis is a multi-step process. Cellular functions required for invasion are attachment, locomotion and directed migration. Regulation of these processes may be independent of cell growth. A carboxylamino-imidazole compound was found to be potent inhibitor of tumor cell attachment, motility, invasion, proliferation, and metastasis. This compound and equivalents thereof constitute a cancer treatment agent of particular use in the treatment of peritoneal carcinomatosis of ovarian cancer.

3 Claims, 8 Drawing Sheets

THERAPEUTIC APPLICATION OF AN ANTI-INVASIVE COMPOUND

BACKGROUND OF THE INVENTION

A class of compounds of the formula:

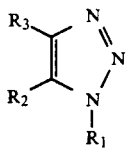

wherein,

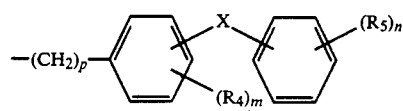

$R_1$ is wherein p if 0 to 2; m is 0 to 4; and n is 0 to 5; X is O, S, SO, $SO_2$, CO, CHCN, $CH_2$ or C=$NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lower carbalboxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R_2$ is amino, mono or diloweralkyl amino, acetaamido, acetimido, ureido, formamido, formimido or guanidino; and $R_3$ is carbamoyl, cyano, carbazoyl, amidino or N-hydroxycarbamoyl; wherein said loweralkyl, loweralkyl containing loweralkoxy and loweralkanoyl groups contain from 1 to 3 carbon atoms, have been determined to be useful for inhibiting proliferation, and invasion and metastasis of malignant tumor cells. Invasion and metastasis, the hallmark of malignancy, is responsible for the lethal effects of cancer. Invasion and locomotion are properties of cancer cells distinct from growth potential. Agents which interfere with these functions selectively in malignant cells have use as agents to prevent or slow metastasis. The compound L651582, (Merck Research Laboratories, U.S. Pat. No. 4,590,201), originally designed as a coccidiostat, was shown previously to inhibit cellular proliferation of normal cells.

In vitro, L651582 inhibited 5-phosphoribosyl pyrophosphate (PRPP) synthesis, and lowered incorporation of formate, hypoxanthine, and adenine without directly inhibiting PRPP synthetase or other enzymes of the de novo and salvage nucleoside synthesis pathways.

Previous data suggested that L651582 inhibits proliferation and inflammation by affecting the biochemical pathways necessary for signal processing in the cell. It is an indirect blocker of the effector enzymes which produce the second messengers necessary to induce growth. These membrane-bound enzymes are activated by coupling to guanine nucleotide binding proteins (G proteins). The antiproliferative effect may be a consequence of the inhibition of those G-protein pathways which mediate the actions of growth factors such as PDGF and TGFα in initiating hydrolysis of the phosphatidyl inositols (Berridge, Ann Rev Biochem, 1987; Allende, FASEB J, 1988; Neer & Clapham, Nature, 1988). The products, inositol trisphosphate and diacylglycerol, stimulate growth by producing changes in intracellular calcium, and intracellular pH, respectively. Data from the inventors' studies indicated that a similar G protein pathway may be required for tumor cell motility, directed migration and invasion. Collectively, the data on the mechanism of action of L651582 led the inventors to propose that L651582 prevents the receptor activation of G proteins, and/or inhibits a class of G proteins from stimulating the effector enzymes necessary for cellular pathways required for cancer, proliferation, invasion and metastasis.

DESCRIPTION OF FIGURES

AMF stimulates random and directed locomotion of 5R ras-transfected rat embryo fibroblasts and A2058 human melanoma cells; the 5R line is tumorigenic and metastatic in nude mice. This motility is markedly inhibited by cell treatment with pertussis toxin (PT) a known modulator of G protein function (PT, 0.5 pg/ml for 2 hr). L651 (0.03≅10 µg/ml) inhibited AMF-stimulated tumor cell motility in a dose dependent manner. Slight inhibition of motility was seen with preincubation times of up to 8 hr; however, optimal inhibition required overnight treatment with L651 (5R, 0 24 hr; A2058 ○ 24 hr, □48 hr). L651 was maintained in the assay system for the duration of the motility assay; cell viability was greater than 95% as determined by trypan blue exclusion. Data are expressed as percent of stimulated motility of untreated cells. Cell treatment with both L651 (1 µg/ml) and PT (0.1 µg/ml) did not result in greater inhibition of motility than either drug alone (data not shown).

■ Cells were preincubated with L651 (0.03–10 µg/ml) for periods of 2 to 48 hr prior to the adhesion assay, and it was present during the 90 min adhesion assay. A small dose dependent inhibition of adhesion to tissue culture plastic was seen after incubations of 2-4 hr of pretreatment. As seen with motility, inhibition of adhesion was maximal after overnight exposure to the drug for 5R (0) and A2058 (○). L651 also decreased cell adhesion to the matrix components laminin and fibronectin (data not shown). Cell spreading was not markedly decreased. Table 1. Evaluation of the reversibility of L651 effect on tumor cell adhesion and motility.

Figure 1:
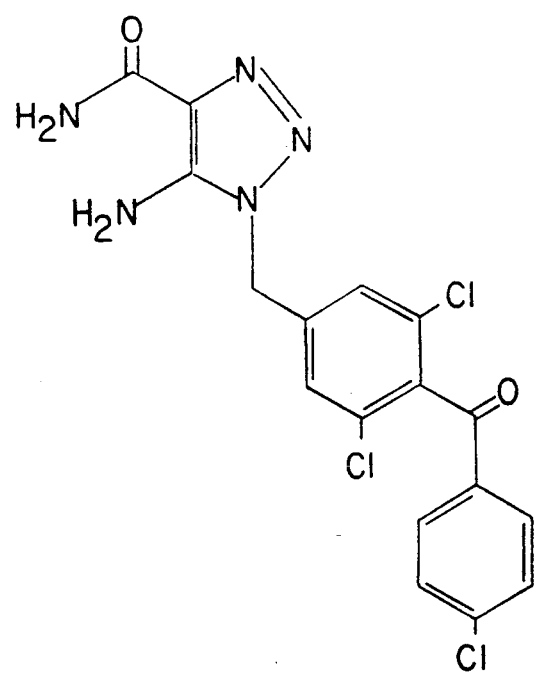
FIG. 1. Structure of L651582.

The motility and adhesion experiments (FIGS. 1 and 2) were done in the continuous presence of L651. This study was done to determine the reversibility of the L651 inhibition of motility and adhesion. A2058 melanoma cells were cultured for 24 hr in standard media (DMEM/10% FCS), washed twice with saline, and cultured with DMEM/10% FCS with (+) or without (−) L651 for 24 hr. Cells were then washed and the treatments were reversed. Control cells were washed and fed with standard media alone at each change point. To evaluate the effects of "washout" of L651 the treated cells (−/+), "washout" cells (+/−), and control cells were studied for motile responses to AMF and ability to adhere to tissue culture plastic (as per FIGS. 1 and 2). Data are expressed as percent of control cell motility and adhesion at the two concentrations of L651 tested. In both cases, the L651 effect could be reversed by 24 hr culture in the absence of L651.

Figure 4:
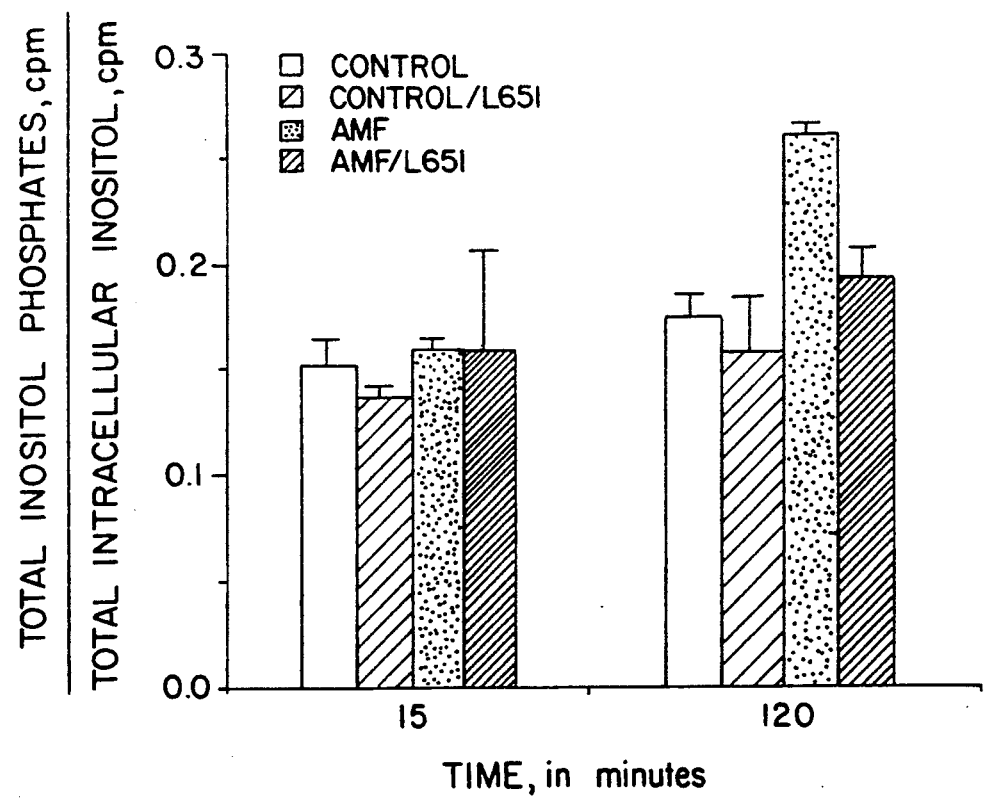

FIG. 4. Effect of L651 on AMF-stimulated generation of total inositol phosphates.

A2058 cells were treated with L651 (1 μg/ml) for 24 hr, washed with PBS, then incubated overnight with media containing $^3$H-inositol into which L651 was not added back. After harvest and 30 min treatment with LiCl (10 mM), treated and control cells were exposed to AMF for 15 and 120 min. Reactions were stopped, lipids extracted, and total inositol phosphates were separated on Dowex anion exchange columns. Pretreatment of the cells with L651 inhibited the formation of inositol phosphates seen in response to AMF at 120 min.

Figure 5:
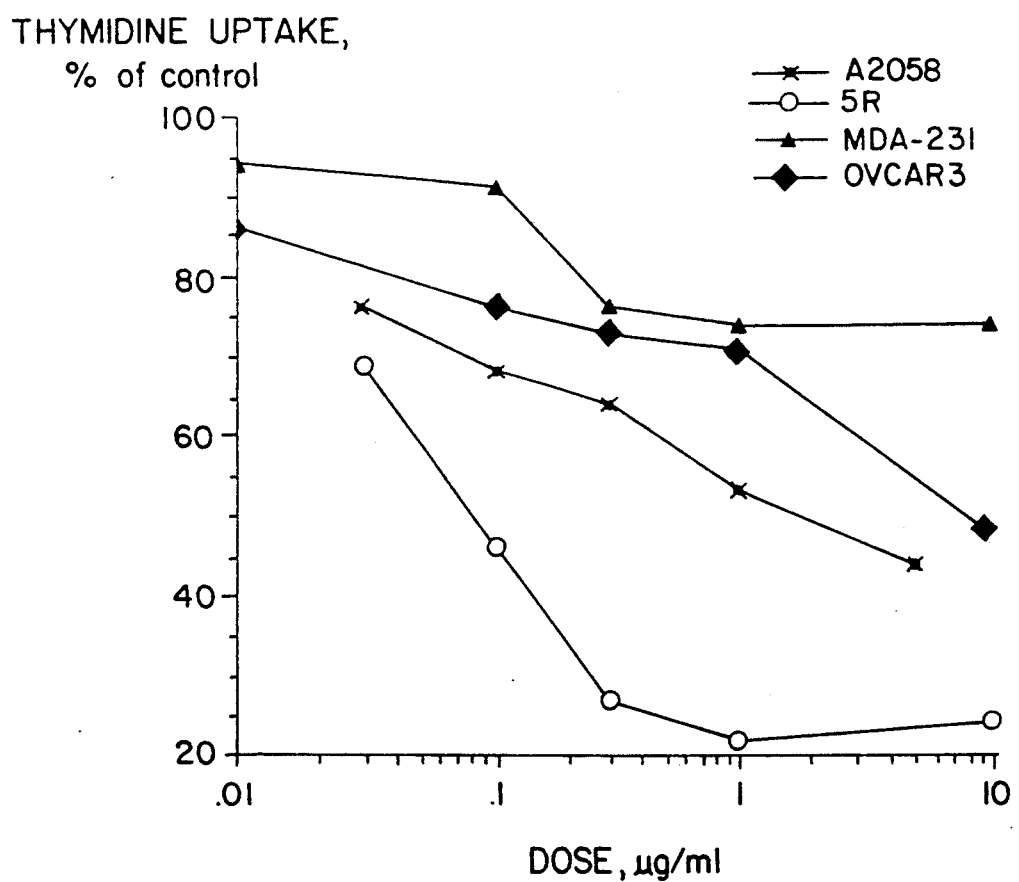

FIG. 5. Dose dependent inhibition of $^3$H-thymidine incorporation by L651.

A2058 (■), 5R (○), MDA-231 human breast cancer (▲), and OVCAR3 human ovarian cancer (◆) cells were grown in 96 well plates to subconfluence, serum-starved, and then treated overnight with serum-containing media into which L651 (0–10 μg/ml) was added. After a 2 hr $^3$H-thymidine pulse, cells were fixed and thymidine uptake determined. Data are expressed as percent of untreated control cell incorporation of labelled thymidine.

Figure 6:
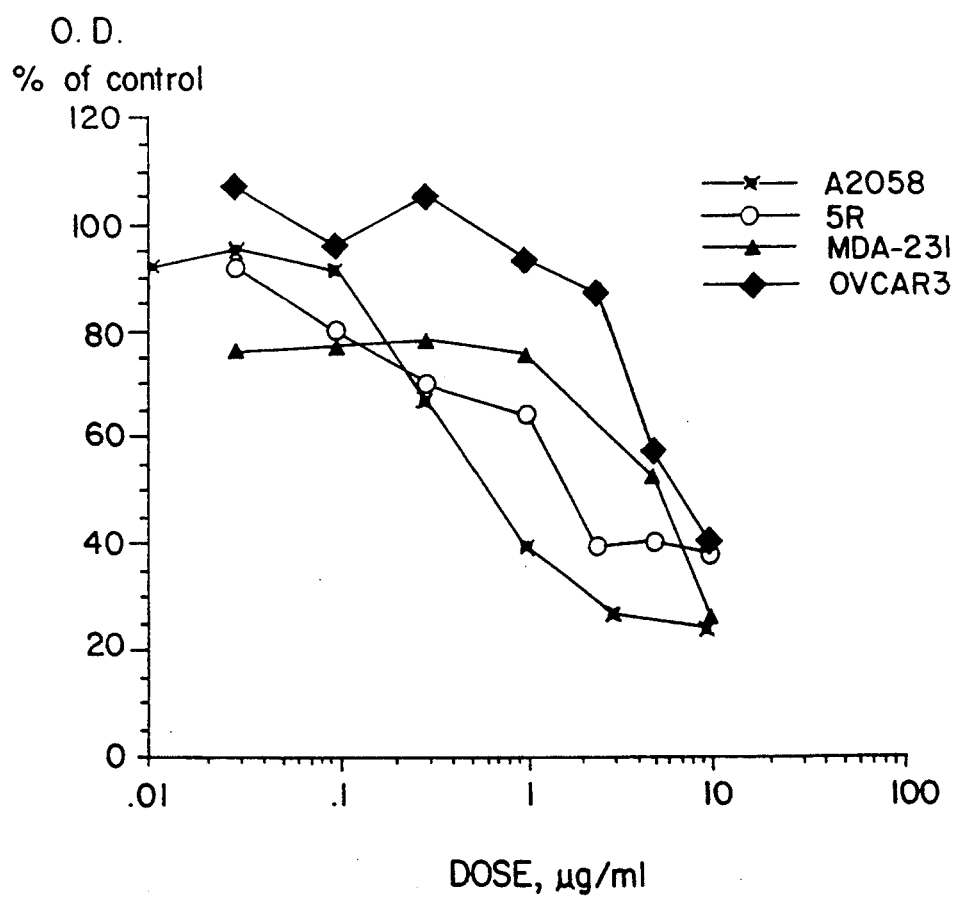

FIG. 6. Dose dependent inhibition of tumor cell proliferation by L651.

A2058 (■), 5R (○), MDA-231 (▲), and OVCAR3 (◆) cells were grown in 24 well plates in serum-containing media into which L651 (0–10 μg/ml) was added. Cells were fixed with methanol and stained with crystal violet nuclear stain. Optical density of eluted stain was determined, and data are expressed as percent of untreated control cell proliferation for each cell type.

Figure 7:
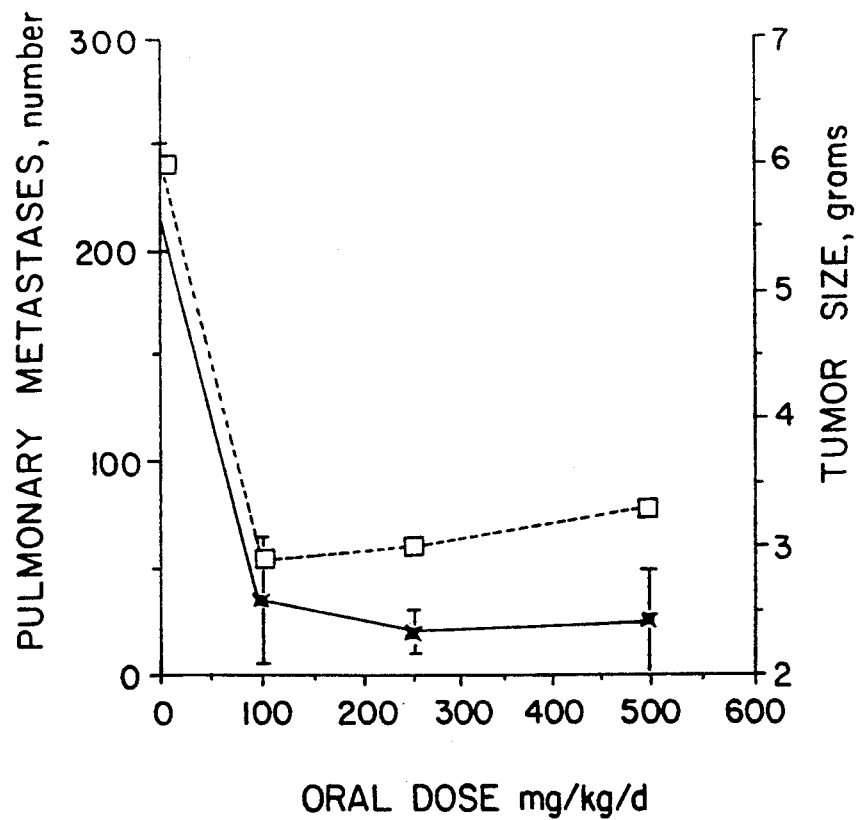
Figure 8:
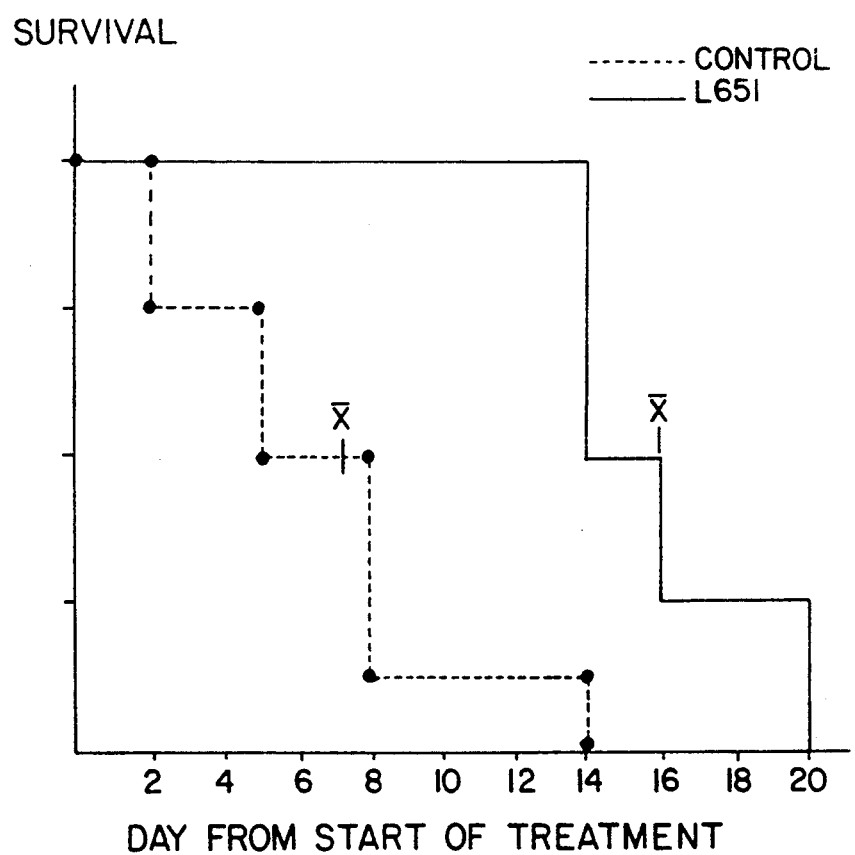

FIG. 7. Increased survival of nude mice bearing metastatic human ovarian carcinoma following treatment with 50 mg/kg/d L651582.

Peritoneal carcinomatosis was induced in nude mice by transplantation of 3.4–10$^7$ human ovarian carcinoma cells (OVCAR3) intraperitoneally. Three weeks later when all mice had distended abdomens due to heavy tumor burden, the mice were divided into two groups. The treatment group received L651, 50 mg/kg/d in 60% DMSO vehicle via daily intraperitoneal (IP) injections; the control group received daily IP vehicle alone. Survival from initiation of treatment was the evaluable endpoint Overall survival from initiation of treatment was extended from 7.25 +/−4.4 days to 16.0 +/−2.5 days.

DESCRIPTION OF THE INVENTION

Studies on the effects of L651582 upon cancer cells have revealed that it has profound effects on tumor cell locomotion, invasion, proliferation and response to motility stimulating factors. Invasion is the hallmark of malignancy. We have shown earlier that tumor cells secrete and respond to the chemoattractant, autocrine motility factor (Liotta et al, Proc Natl Acad Sci USA, 1986). The motile response to AMF is mediated by a pertussis toxin sensitive G protein complex as indicated by the profound inhibitory effect of pertussis toxin on stimulated motility (Stracke et al, Biochem Biophys Res Comm, 1987). It is now known also that AMF stimulates the generation of inositol-trisphosphate in reactions which are inhibited by pertussis toxin, suggesting the activation of a phosphatidyl inositol bisphosphate-specific phospholipase C (Kohn et al, Proc Amer Assoc Cancer Res, 1988). This finding was the first evidence linking a biochemical pathway to tumor cell locomotion. The motility associated with protein mediated activation of phospholipase C is now seen as part of the metastatic cascade. Agents which can interrupt this important pathway which mediates both growth and motility, provide valuable new cancer treatment modalities. Compounds of formula I are the first in a new class of anti-invasion, anti-proliferative agents which evidence a direct effect on G protein-mediated signal metastatic transduction.

It has been well established in the cancer biology field that tumor cell attachment and motility are key functions required for invasion and metastasis. Compounds of formula I specifically inhibit these functions. L651582, a compound of formula I, has been shown to inhibit de novo and salvage nucleoside synthesis, vanadate stimulated inositol trisphosphate release from MDBK cells, arachidonic acid metabolism in fMLP-stimulated PMNs resulting in the decrease metabolites of both the cyclooxygenase and lipoxygenase pathways, and to prevent the release of labelled calcium from these intact cells. However, L651582 did not affect the enzymes involved in these pathways directly. These effects were prevalent in the micromolar concentration range. L651582 appears to exert its inhibitory activity at or near the site of G protein interaction with either receptor or effector enzyme, and thus may successfully inhibit crucial tumor cell functions. Receptor-mediated functions such as motility, invasion, adherence, and growth may be interdicted at the signal transduction step by compounds disclosed herein.

It has now been found that compounds of formula I can be used as anti-invasion and anti-proliferative agents in the treatment of malignant disease, particularly peritoneal carcinomatosis of solid tumors such as ovarian cancer. L651582, at concentrations of 1–10 pM, inhibited AMF-stimulated motility of several tumor lines of human and rat origin, and decreased the adherence of these lines to tissue culture plastic; these effects were reversible. This class of compounds also diminishes the stimulatory effect of AMF on phosphoinositide metabolism. In testing, L651582 inhibited growth of human melanoma, breast, ovarian, prostatic and bladder carcinomas, human T-cell lymphomas, murine leukemia, and ras-transfected rat embryo fibroblast cells, in clonogenic assays. In addition to the anti-proliferative effect, L651582 was found to profoundly inhibit adhesion, growth, and stimulated motility, requirements for tumor invasion and metastasis. In an animal model of human ovarian peritoneal carcinomatosis, L651582 transiently decreased the magnitude of malignant ascites leading to a 220% increase in overall survival.

Because human ovarian carcinoma has the insidious propensity to spread within the peritoneal cavity and to invade multiple abdominal organs, peritoneal carcinomatosis results in high rate of mortality. The ability of compounds of formula I to inhibit attachment, invasion and proliferation, is especially useful in treating ovarian carcinomas. L651582 was tested in an animal model which closely approximates the pathologic events in human ovarian carcinoma. In this model, human ovarian carcinoma cells are injected intraperitoneally into nude mice. Human tumor cells rapidly migrate and invade the abdominal cavity in a fashion identical to the human patient. In this animal model system, all the mice rapidly succumb to abdominal metastasis. When the mice bearing intraperitoneal carcinomatosis were treated with L651582, a highly significant prolongation of survival was achieved (FIG. 7) verifying the utility of this compound in this field of use.

Studies which show L651582 to be an effective inhibitor of adhesion, motility, and growth have demonstrated the effects of such compounds on metastatic ovarian carcinomatosis in a well-characterized assay.

Compounds of formula I can be administered, for example, by intravenous infusion, orally, topically, intraperitoneally, or intrathecally for treatment of lymphomas, leukemias, and all solid tumors. The compounds could be applied in a suitable vehicle for the local and topical treatment of cancer. Tumors such as basal cell carcinoma and Kaposi's sarcoma could be treated by topical administration of the agents taught herein. Prevention of tumor recurrence by administration of the composition in a manner intended to reach the particular site where such cells are proliferating would be most advantageous. For example, intraperitoneal administration would be a preferred means of treating tumors known to cause peritoneal carcinomatosis. Intravesical treatment of transitional cell carcinoma and topical treatment of mycosis fungoides are further examples of site-directed treatment. Systemic administration may be accomplished by continuous infusion, bolus parenteral treatment, or release from an implanted slow release depot. It is obvious that this agent can supplement treatment of cancer by any conventional therapy including cytotoxic agents and biologic response modifiers. The method disclosed may be used in any malignancy as a means of treatment to prevent the transition from in situ to invasive carcinoma.

The use of compositions taught herein is not restricted to use in treatment of malignancies. Disease conditions resulting from localized spread of diseased cells may be advantageously used in treatment of such conditions as endometriosis.

EXAMPLE 1

Materials: Crystalline L651582 powder was supplied by Merck Research Laboratories. A 20 mg/ml stock solution was made in DMSO and aliquots were stored at $-70°$ C. For use, a 10 μg/ml solution was prepared daily in media (DMEM), and serial dilutions were made as needed. The range of concentrations used was 0.03 to 10.0 μg/ml. The DMSO vehicle was diluted at least one thousand fold and was inert in the experiments described herein (data not shown).

$^3$H-inositol (specific activity 105 mCi/mg) and 3$^3$H-thymidine (specific activity 102 mCi/mg) were purchased from Amersham (Arlington Heights, IL), and Dowex anion exchange resin 1-X8, formate form, was from BioRad (Rockville Center, NY). The motility chamber and nucleopore filters (8 μ, polyvinylpyrrolidone-free) were from Neuro Probe, Inc. (Cabin John, MD). Type IV collagen was obtained from Collaborative Research (Bedford, MA). Phenol red-free IMEM with low inositol [2.7 nM] was obtained from the NIH media unit. Other reagents were reagent grade.

Cells, culture, and production of autocrine motility factor: The A2058 human melanoma cell line was maintained in subconfluent culture with Dulbecco's Modified Essential Medium (DMEM) containing 10% fetal calf serum (FCS). AMF was prepared from A2058 cells as described (Stracke et al, Biochem Biophys Res Comm, 1987). Briefly, cells were grown in serum-free DMEM containing 0.01% BSA for 48 hr; the conditioned media was concentrated using an Amicon filtration system which excludes compounds of molecular weight greater than 30 KD. This AMF was used for all of the assays described. The activated H-ras transformed (diploid) rat embryo fibroblast line, 5R, was grown under the same conditions. This line has been shown previously to express tumorigenic and metastatic phenotypes. MDA-MB-231 human breast carcinoma line was purchased from ATCC (Rockville, MD) and was maintained as described above. The OVCAR3 cells were a generous gift of Dr. Robert Ozols (Fox Chase Cancer Center, Philadelphia, PA) and were cultured in RPMI with 10% FCS.

Cell motility and adhesion: The cell motility assay has been described (Stracke et al, Biochem Biophys Res Comm, 1987). Subconfluent cells were harvested with trypsin-EDTA and were allowed to recover for 1 hr at room temperature; 5R were harvested with 2 mM EDTA in PBS without divalent cations. Cells were resuspended in serum-free media containing 0.1% BSA; this DMEM/0.1% BSA was used as the control for all subsequent assays. The assays were performed in triplicate using a 48-well chemotaxis chamber with 8 μ Nucleopore, type IV collagen-coated filters. The chambers were incubated for 4 hr, and the filters removed and stained. Cell migration was quantitated using laser densitometry which has been shown to be linearly correlated with the number of migrating cells. The effect of L651582 [0.03–5.0 μg/ml] on the motility of A2058 and 5R cells was studied. Cells were preincubated with L651582 for up to 48 hr and then assayed for their motile response to AMF. Cell viability determined by trypan blue exclusion averaged greater than 96%. Cells exposed to various concentrations of L651582 were tested for their response to AMF vs. control; the drug remained present during the motility and adhesion assays. Percent stimulated motility (in densitometer units) is defined as:

$$\frac{\text{(AMF stimulated-control)}_{L651}}{\text{(AMF stimulated-control)}_{untreated}}$$

An adhesion assay was developed using tissue culture plastic petri dishes as the substrate. Aliquots of similarly treated cells were plated in triplicate onto the dishes and incubated for 90 min at 37° C. Poorly and nonadherent cells were washed off gently with PBS, and adherent cells were stained. Adherence was quantitated using the laser densitometer, and data calculated as percentage of the control adherence.

Phosphatidyl inositol (PI) metabolism assay: The effects of L651582 on AMF-stimulated PI metabolism were studied. A2058 cells were incubated with 1.0μg/ml L651582 for 24 hr prior to overnight labelling; an untreated control flask was maintained in parallel. After the preincubation period, the control and treated cells were labelled overnight with $^3$H inositol in serum-free, low inositol IMEM (LI-IMEM). L651582 was not added back during the labelling period or during the subsequent turnover assay. Cells were then harvested, suspended and incubated in LI-IMEM containing 10 mM LiCl for 30 min. At the initiation of the metabolism assay, AMF or serum-free media control was added to aliquots of 100,000 cells and these aliquots were incubated at 37° C for 15 and 120 min. At the completion of the incubation period, the cells were washed twice with ice cold PBS and then extracted with chloroform:methanol (1:2). The total inositol phosphates were removed using Dowex anion exchange column chromatography eluted with ammonium formate 1.0 M/formic acid 0.1 M buffer. Total inositol phosphates and unincorporated total intracellular $^3$H-inositol were quantitated by ligand scintillation counting. Data are expressed as a ratio of total inositol phosphates to total unincorporated $^3$H-inositol and standard errors for these ratios were calculated.

Growth: Growth inhibition was quantitated using two independent methods: $^3$H-thymidine labelling, and crystal violet nuclear staining. Growth studies were done with A2058, 5R, OVCAR3, and MDA-231 cells. An initial aliquot of 15,000 cells were plated in 96 well plates for the thymidine incorporation assay. After serum-starvation, cells were fed with serum-containing media to which incremental doses of L651582 was added. Twenty-four hours later, the cells were pulsed with $^3$H-thymidine for 2 hr, and TCA-precipitable counts were extracted with EtOH/ether followed by solubilization with 0.2 M NaOH. Percent growth inhibition was determined. In the clonogenic assay, aliquots of 50,000 cells per well (24 well plates) were grown under standard tissue culture conditions in the presence of increasing doses of L651582. After the culture period, cells were gently washed with PBS, fixed, and stained with 0.5% crystal violet in 20% MeOH. Excess stain was removed with tap water. Bound stain was eluted with a 1:1 (v/v) solution of 0.1 N Na citrate (pH 4.2) and 100% EtOH. Optical density of aliquots of the eluant were determined at 540 nm; data are expressed as percent of control O.D.

Animal survival study: Six-week-old athymic mice were inoculated intraperitoneally with 3.4–10$^7$ OVCAR3 human ovarian cancer cells. After a three-week period, all animals had grossly distended abdomens due to OVCAR3 ascites. Two groups of animals (N =4) were paired for relative severity of ascites and treatment was initiated. L651582, 50 mg/kg/d in 60% DMSO (200 µl aliquot) a vehicle alone was administered intraperitoneally once daily. Overall survival from start of treatment was the study endpoint. Relative survival improvement was calculated as mean treatment group survival divided by mean control group survival.

Results

Figure 2:
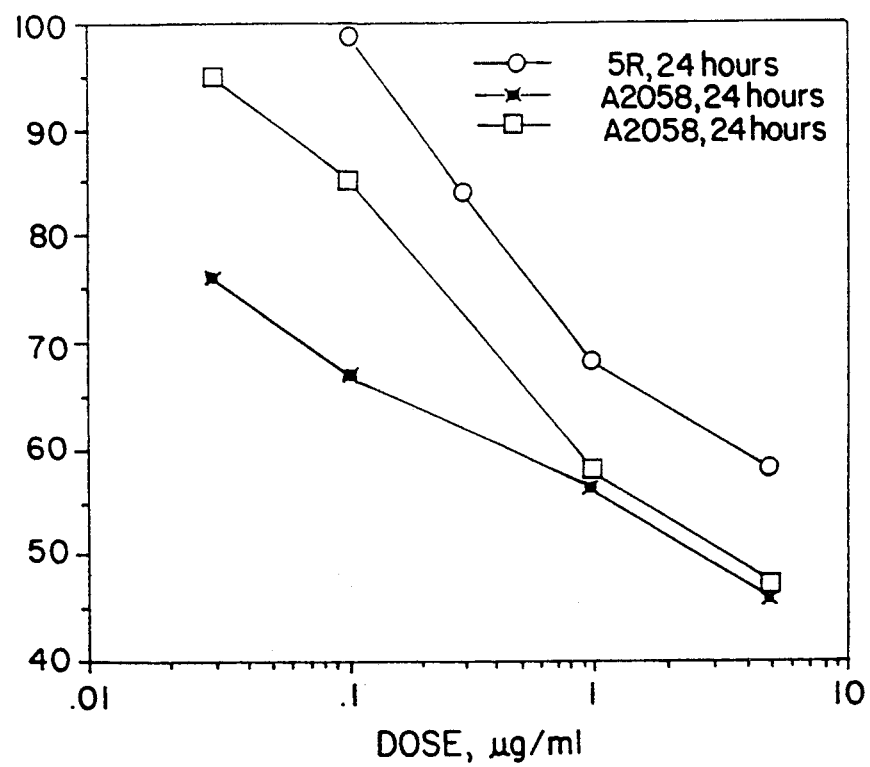
FIG. 2. Dose dependent inhibition of L651 on autocrine motility factor (AMF)-stimulated chemotaxis.
Figure 3:
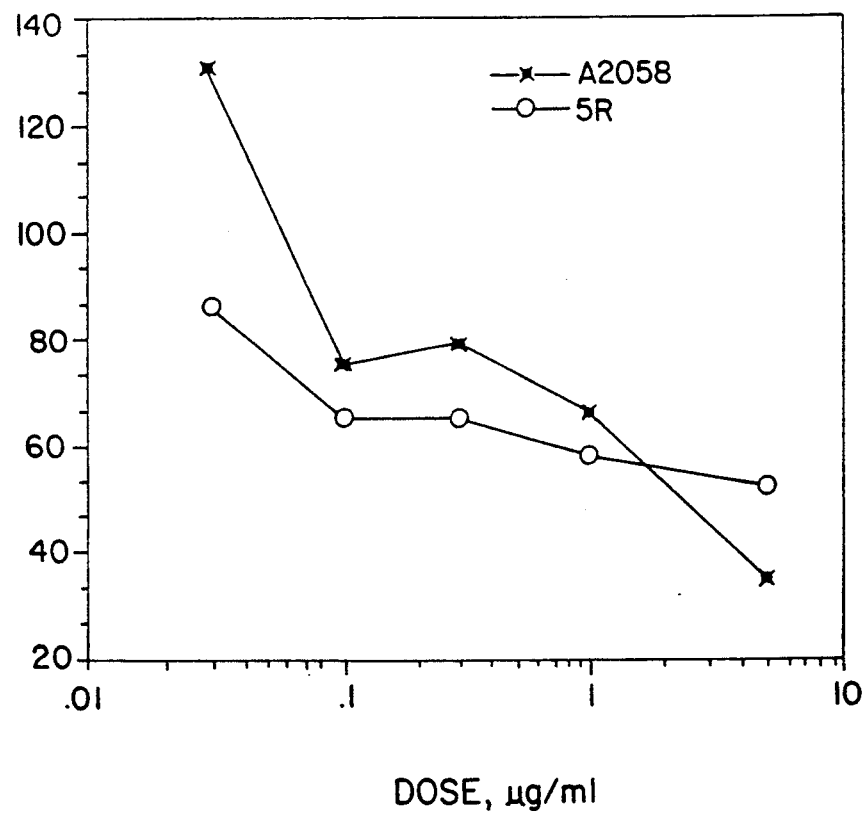
FIG. 3. Dose dependent inhibition of L651 on tumor cell adhesion to tissue culture plastic.

Tumor cell motility and adhesion: The effect of preincubating cells with L651582[0.03–5.0 µg/ml] was studied using A2058 or 5R cells in a modified Boyden chamber motility system. A slight decrease in AMF-stimulated motility was seen after 2–4 hr of exposure to L651582 (data not shown); overnight preincubation yielded reproducible dose-dependent decreases in stimulated motility of up to 55% as shown in FIG. 2. Greater increments in the time of exposure (up to 48 hr) did not result in further inhibition of AMF-stimulated motility. The motile responses to AMF of two human breast cancer cell lines SKBR and MDA-231 also were inhibited after overnight exposure to L651582 (data not shown). The effect of L651582[0.03–5.0 µg/ml] on tumor cell adhesion to tissue culture plastic was studied. FIG. 3 demonstrates the dose-dependent inhibition of A2058 and 5R cell adhesion. After as little as 4 hr of preincubation inhibition of adherence was seen but was of lesser magnitude than after overnight treatment. The maximum dose studied, 5 µg/ml, yielded the greatest inhibition, 50–60% of control. We studied the potential reversibility of L651582 on motility and adhesion by removing the drug from the incubation media (Table 1).

Cells were incubated with L651582 or control for 24 hr, washed twice with PBS, and further incubated for 24 hr with either control or L651582, respectively. Cells were harvested and studied in both motility and adherence assays. The inhibition of tumor cell motility and adhesion were reversed by removal of L651582 from the culture media.

Phosphoinositide metabolism: L651582 has been shown to block phosphatidyl inositol (PI) hydrolysis in studies with normal cell systems, including the neutrophil (D. Hupe, Merck Research Laboratories, unpublished observations). It had previously been demonstrated that AMF stimulates PI metabolism in A2058 cells, and that PI metabolism parallels motility in dose response experiments. The effect of L651582 on this biochemical response to AMF is now shown. Cells were pretreated with L651582[1.0 µg/ml] for 24 hr prior to overnight labelling with $^3$H-inositol. L651582 was not reintroduced during labelling nor during the metabolism assay. FIG. 4 shows L651582 significantly inhibited AMF-stimulated PI hydrolysis. The degree of inhibition is similar to the inhibition of motility at this dose (45%). These data also suggested that this biochemical effect of L651582 on PI turnover was not easily reversible in contrast to the effect on motility and adhesion, as the drug was not present during the 24 hr labelling period prior to or during the assay. No appreciable drug effect was seen on the treated, unstimulated cells. This partial inhibition by L651582 of AMF-stimulated phosphoinositide metabolism, which was shown previously also to be partially inhibited by pertussis toxin suggests that the site of action of L651582 may be at or near the G protein associated with phospholipase C.

Growth: L651582 indirectly inhibits both the de novo and salvage nucleoside synthesis pathways. The effects of L651582 on growth were studied in four different tumor cell lines: A2058 melanoma, MDA-231 breast, and OVCAR3 ovarian carcinomas, and the 5R transformed rat embryo fibroblast. Two independent approaches were used to assess cell proliferation: $^3$H-thymidine incorporation and a clonogenic assay using crystal violet nuclear staining. The clonogenic approach was used because the potential effect of L651582 on pyrimidine (specifically, thymidine) metabolism was unknown. FIG. 5 shows that after 24 hr exposure to L651582, inhibition of $^3$H thymidine incorporation as a marker of de novo DNA synthesis was seen in all cell lines. In the clonogenic assay, the length of exposure to L651582 was adjusted for the doubling time of the different lines. FIG. 6 presents the dose-dependent inhibition of clonogenic tumor cell proliferation expressed as percent of untreated controls. The degree of inhibition varied with the cell type, and was maximal (24%) for the A2058 line after 96 hr in culture. L651582 showed significant antiproliferative properties against tumor cells, with average ED$_{50}$ of 1–10 µM, in addition to the previously described effects against normal cells.

Animal survival study: The OVCAR3 human ovarian cancer animal model accurately approximates the clinical presentation of stage III ovarian cancer of peritoneal carcinomatosis. Untreated, OVCAR3 ascites is lethal to nude mice. We report the marked survival advantage seen in OVCAR3 bearing nude mice treated with L651582 50 mg/kg/d. The heavily laden mice were split into two groups for L651582 treatment or vehicle alone. Overall survival was prolonged from 7.25±4.4 days to 16.0±2.5 days, 220% over control.

It has been found that compositions for use by the method of the invention should preferably, be desolved in a hydrophobic solution. Examples of addatives that may be particularly useful are DMSO. polyethylene glycol. and lipids. Particularly preferred are lipid carriers.

TABLE

|  | 5 ug/ml +/− | 5 ug/ml −/+ | 1 ug/ml +/− | 1 ug/ml −/+ |
| --- | --- | --- | --- | --- |
| Motility | 94 | 27 | 97 | 59 |
| Adhesion | 96 | 37 | 106 | 33 |

We claim:

1. A method of treating peritoneal carcinomatosis of solid tumors in mammals, said method comprising administering to said mammals an anti-peritoneal carcinomatosis effective amount of a compound of the formula:

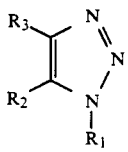

wherein, $R_1$ is

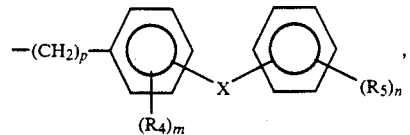

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano;

$R_4$ and $R_5$ are independently halogen, cyano, trifluoromethyl, loweralkanoyl, nitro, loweralkyl, loweralkoxy, carboxy, lowecarbalkoxy, trifluoromethoxy, acetamido, loweralkylthio, loweralkylsulfinyl, loweralkylsulfonyl, trichlorovinyl, trifluoromethylthio, trifluoromethylsulfinyl or trifluoromethylsulfonyl;

$R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein said loweralkyl, loweralkyl containing loweralkoxy and loweralkanoyl groups contain from 1 to 3 carbon atoms.

2. The method of claim 1, wherein said solid tumor is an ovarian tumor.

3. The method of claim 1, wherein p is b 1, m is 2, and n is 1; X is CO; $R_4$ and $R_5$ are both chlorine; $R_2$ is amino; and $R_3$ is carbamoyl.

* * * * *